US009539225B2

(12) United States Patent
Tanaka et al.

(10) Patent No.: US 9,539,225 B2
(45) Date of Patent: Jan. 10, 2017

(54) ANEMIA OF CANCER IMPROVING/PROPHYLACTIC AGENT

(71) Applicant: SBI Pharmaceuticals Co., Ltd., Tokyo (JP)

(72) Inventors: Tohru Tanaka, Tokyo (JP); Motowo Nakajima, Tokyo (JP); Fuminori Abe, Tokyo (JP); Satofumi Kawata, Tokyo (JP); Kiwamu Takahashi, Tokyo (JP)

(73) Assignee: SBI Pharmaceuticals Co., Ltd., Tokyo (JP)

( * ) Notice: Subject to any disclaimer, the term of this patent is extended or adjusted under 35 U.S.C. 154(b) by 39 days.

(21) Appl. No.: 14/350,675

(22) PCT Filed: Oct. 5, 2012

(86) PCT No.: PCT/JP2012/076020
§ 371 (c)(1),
(2) Date: Apr. 9, 2014

(87) PCT Pub. No.: WO2013/054770
PCT Pub. Date: Apr. 18, 2013

(65) Prior Publication Data
US 2014/0288173 A1 Sep. 25, 2014

(30) Foreign Application Priority Data

Oct. 12, 2011 (JP) .................................. 2011-225383
Mar. 30, 2012 (JP) .................................. 2012-081346

(51) Int. Cl.
| | | |
|---|---|---|
| *A61K 31/195* | (2006.01) | |
| *A01N 37/12* | (2006.01) | |
| *A01N 37/44* | (2006.01) | |
| *A61K 31/295* | (2006.01) | |
| *A61K 31/197* | (2006.01) | |
| *A61K 33/26* | (2006.01) | |
| *A61K 31/216* | (2006.01) | |
| *A61K 31/222* | (2006.01) | |
| *A61K 33/06* | (2006.01) | |
| *A61K 33/30* | (2006.01) | |

(52) U.S. Cl.
CPC ........... *A61K 31/195* (2013.01); *A61K 31/197* (2013.01); *A61K 31/216* (2013.01); *A61K 31/222* (2013.01); *A61K 31/295* (2013.01); *A61K 33/06* (2013.01); *A61K 33/26* (2013.01); *A61K 33/30* (2013.01)

(58) Field of Classification Search
CPC  A61K 2300/00; A61K 31/197; A61K 31/295; A61K 33/06; A61K 33/26; A61K 33/30; A61K 31/22; A61K 31/195; A61K 31/216; A61K 31/222
USPC ................. 514/502, 561; 562/567
See application file for complete search history.

(56) References Cited

U.S. PATENT DOCUMENTS

| | | | | |
|---|---|---|---|---|
| 9,018,257 | B2 * | 4/2015 | Rephaeli | A61K 41/0061 |
| | | | | 514/547 |
| 2004/0234555 | A1 | 11/2004 | Oshida et al. | |
| 2014/0256806 | A1 * | 9/2014 | Tanaka | A61K 31/197 |
| | | | | 514/502 |
| 2015/0290159 | A1 * | 10/2015 | Tanaka | A23L 1/30 |
| | | | | 514/502 |

FOREIGN PATENT DOCUMENTS

| | | |
|---|---|---|
| CA | 2793153 A1 | 9/2011 |
| CN | 1538839 A | 10/2004 |
| CN | 102164596 A | 8/2011 |
| EP | 1413303 A1 | 4/2004 |
| JP | 2003-040770 A | 2/2003 |
| JP | 2009/298739 A | 12/2009 |
| JP | 2011-016753 A | 1/2011 |

OTHER PUBLICATIONS

Berkovitch-Luria et al., "A multifunctional 5-aminolevulinic acid derivative induces erythroid differentiation of K562 human erythroleukemic cells", Available online Jun. 13, 2012, European Journal of Pharmaceutical Sciences, 47(1), pp. 1-294.*
Di Venosa et al., "Distribution of 5-aminolevulinic acid derivatives and induced porphyrin kinetics in mice tissues", 2006, Cancer Chemother. Pharmacol., 58(4), pp. 478-486.*
International Search Report mailed Dec. 11, 2012, in corresponding International Patent Application No. PCT/JP2012/076020, with English translation (4 pages).
Ouchi, Kiyota, "History of digestive surgery of the laboratory and developmental mechanism of cancerous anemia"; The Japanese Journal of Gastroenterological Surgery, vol. 11, No. 11, 1978; pp. 885-896, with a Concise explanation on Relevance between claims and the literature (1 page).
Article entitled "The risk of 'cancerous anemia' was increased by ESA", in New Current, vol. 22, No. 18, 2011; pp. 7-8 (3 pages), with Concise explanation on Relevance between claims and the literature (1 page).
EPO Communication ("Office Action") dated Mar. 6, 2015 (1 page), with an Extended European Search Report dated Feb. 24, 2015, from European Patent Application No. EP-12840143 (5 pages).
Database WPI, Week 201003; Thomson Scientific, London, GB; AN 2009-S70615; XP002736347 (4 pages). [Corresponds with JP-2009298739.].
First Office Action issued Feb. 3, 2015, by the State Intellectual Property Office of the People's Republic of China in corresponding Chinese Patent Application No. CN 2012-80060371.8, with English translation (13 pages).

(Continued)

Primary Examiner — My-Chau T Tran
(74) Attorney, Agent, or Firm — Osha Liang LLP

(57) ABSTRACT

A method for ameliorating and/or preventing cancerous anemia includes administering to a subject in need thereof an agent containing 5-aminolevulinic acid (ALA) or a derivative thereof, or a salt thereof. Preferably, these ALAs contain a metal-containing compound, such as sodium ferrous citrate. The above-mentioned ALAs, ALA; various esters such as ALA methylester, ALA ethylester, ALA propylester, ALA butylester, and ALA pentylester; and hydrochlorides, phosphates, and sulfates, and the like of these ALA esters are preferred examples.

10 Claims, No Drawings

(56) References Cited

OTHER PUBLICATIONS

Official Action dated Sep. 7, 2015, issued by the Japan Patent Office in corresponding Japanese Patent Application No. JP2013-538532 (4 pages), with Google English machine-translation (3 pages).
Gozzard, David, "When is high-dose intravenous iron repletion needed? Assessing new treatment options"; Drug Design, Development and Therapy, vol. 20, No. 5 (2011); pp. 51-60.
Mystakidou, Kyriaki, et al., "Evaluation of Epoetin Supplemented with Oral Iron in Patients with Solid Malignancies and chronic Anemia not Receiving Anticancer Treatment"; AntiCancer Research, vol. 25, No. 5 (2005); pp. 3495-3500.
Office Action issued in corresponding Taiwanese Application No. 101137452 dated Jan. 7, 2016 (4 pages).
Y. J. Chen, et al.; "Evaluation of 8-Aminolevulinic Acid on Serum Iron Status, Blood Characteristics, Egg Performance and Quality in Laying Hens"; Asian-Aust. J. Anim. Sci.; vol. 21, No. 9; pp. 1355-1360; Sep. 2008 (6 pages).

* cited by examiner

ANEMIA OF CANCER IMPROVING/PROPHYLACTIC AGENT

CROSS REFERENCE TO RELATED APPLICATIONS

This is a national stage application based on PCT/JP2012/076020, filed on Oct. 5, 2012, which claims priority to Japanese Patent Application Nos. 2011-225383, filed on Oct. 12, 2011, and 2012-081346, filed on Mar. 30, 2012. This application claims the priority of these prior applications and incorporates their disclosures by reference in their entireties.

TECHNICAL FIELD

The present invention relates to an agent for ameliorating and/or preventing cancerous anemia, and more specifically, relates to an agent for ameliorating and/or preventing cancerous anemia comprising 5-aminolevulinic acid (ALA) or a derivative thereof, or a salt thereof.

BACKGROUND ART

Cancerous anemia is an anemia specific to cancer patients, and is known to be an anemia largely different to generally-known iron-deficiency anemia and renal anemia. It is known that, although differing in degree, actually 80% of people suffering from cancer become cancerous anemic and the anemic symptoms worsen with cancer progression, and that anemia progresses further by anticancer drugs and radiation treatment. Cancerous anemia has become a major problem since it greatly reduces the quality of life of cancer patients.

Among that considered to be cancerous anemia, although examples of iron-deficiency anemia caused by bleeding from cancer sites are known, such is only a small portion, and the cause of most cancerous anemia is still unknown. According to Ouchi et al., although the mechanism of cancer secreting an anemia inducing factor to hemolyze red blood cells has been proposed and studied, the anemia inducing factor has still not been specified (for example, refer to Non-Patent Document 1).

In contrast, although iron-deficiency anemia in most cases is resolved by the administration of an iron supplement, iron supplements rarely show effects for cancerous anemia. Also, iron supplements are rarely used for cancerous anemia for the reason that iron promotes cancer growth.

On the other hand, it is known that the cause of renal anemia is reduction in the production of erythropoietin, which is a hematopoietic factor that promotes differentiation to red blood cells. Compounds which stimulate erythropoietin, derivatives thereof, and erythropoietin receptors have been developed and are in practical use. However, since examples in which reduction of the concentration of erythropoietin has occurred are not known for normal cancerous anemia patients, it is considered that the causes of renal anemia and cancerous anemia are completely different.

Regardless of this, many attempts have been made to use erythropoietin for the symptomatic therapy of cancerous anemia. However, although small improvement in anemia has been seen for cancerous anemia which has worsened by some anticancer drugs and radiation treatment, permission has been cancelled in the United States of America since the survival rate of the administered group was less than the placebo group, and approval has been denied in Japan. It has been reported that, according to the analysis of the experimental results, the incidence rate of thrombosis and vascular system disorder in the administered group was high, and tumor progression was promoted (for example, refer to Non-Patent Document 2).

Accordingly, although blood transfusion has been performed as symptomatic therapy in the treatment of cancerous anemia, blood transfusion has the risk of various infectious diseases and there is also the problem of iron repletion. Furthermore, since the costs are high and blood supply is limited, there is a desire for the development of an agent for ameliorating cancerous anemia and an agent for preventing cancerous anemia.

CITATION LIST

Non-Patent Literature

Non-Patent Document 1
  The Japanese Journal of Gastroenterological Surgery 11(11) 885-896, 1978
Non-Patent Document 2
  New Current 22(18) 7-8, 2011

SUMMARY OF THE INVENTION

Problems to be Solved by the Invention

The object of the present invention is to provide an agent for ameliorating and/or preventing anemia, which is useful in the amelioration and/or prevention of cancerous anemia, and which can improve the quality of life of a cancerous anemia patient without advancing cancer progression.

Means for Solving the Problems

The present inventors, after detailed investigation of the large volume of data regarding known research and therapeutic agents for anemia in general, and further examination of the differences between cancerous anemia and other types of anemia, reached the conclusion that the cause of anemia in cancer patients is not a hematopoietic factor or iron. Screening for compounds that can ameliorate and/or prevent cancerous anemia other than a hematopoietic factor was thus begun, and as a result of much research, it was found completely unexpectedly that ALA has an effect of ameliorating cancerous anemia.

In the diagnosis and therapy fields of cancer or the like, ALA is widely used in photodynamic therapy (PDT) and photodynamic diagnosis (PDD). Although ALA is a common precursor of heme system compounds, in cancer cells, it is known that heme is not produced and protoporphyrin IX (PPIX), which is a precursor of heme system compounds, accumulates even if ALA is administered. PDD is possible when the accumulated PPIX is exposed to light since fluorescence is produced therefrom, and PDT is possible since active oxygen is produced in the presence of oxygen. Since cancerous anemia is specific to cancer patients, the relationship between ALA and the PDT or PDD effect is thought of. However, light exposure is not necessary for the present invention.

Although heme is not produced in cancer cells by ALA as mentioned above, since heme is an important constitutional element of red blood cells, it adds up to hematogenesis not being achieved for hematopoietic cell cancer even if ALA is added. However, since cancerous anemia is also seen in patients with cancer other than hematopoietic cell cancer, it is difficult to consider that heme not being produced from ALA in cancerated hematopoietic cells becomes a direct cause of cancerous anemia.

Regarding the relationship between anemia and ALA, it is known that ALA is effective regarding the prevention of anemia in piglets (refer to Japanese Patent No. 4754731). It was reported that anemia in piglets results from hematogenesis not being able to keep up with rapid growth, and the addition of ALA is effective as one compound necessary in hematogenesis. Since growth is not increased for cancerous anemia, it is difficult to consider that ALA will improve cancerous anemia by the same mechanism.

As mentioned above, it cannot be conceived from known information that ALA is effective for cancerous anemia. Also, although discussion of why ALA is effective in the amelioration and/or prevention of cancerous anemia is difficult at the present point in which the cause of cancerous anemia has not been specified, it can be considered to probably be related to suppression of the production of the anemia inducing factor and inhibiting hemolyzation of red blood cells by the same factor in the hypothesis by Ouchi et al. (refer to Non-Patent Document 1). However, further study is necessary for clarification of the action mechanism. Furthermore, it was found that the effects of the present invention are increased by a metal-containing compound such as an iron compound being coordinated with ALA. When minerals are sufficient or when such are ingested separately, there are no problems with the administration of ALA alone. Among minerals, there is a tendency for iron to be insufficient in Japanese, whose amount of consumed red meat is small compared to other countries. For this reason, although iron is simultaneously added in the Examples for Japanese, it is not necessary when the target is a person having sufficient stored iron. Also, although it is widely known that ALA is metabolized to porphyrin, and then shows PDT and PDD activity when exposed to light, light is not necessary for the agent for ameliorating cancerous anemia of the present invention.

The present inventors, after much further thorough study regarding administration methods, combination with other components and other agents, administration amounts, and the like, established an agent for ameliorating and/or preventing cancerous anemia including ALA, thus leading to completion of the present invention.

That is, the present invention relates to (1) an agent for ameliorating and/or preventing cancerous anemia containing a compound represented by the following formula (I):

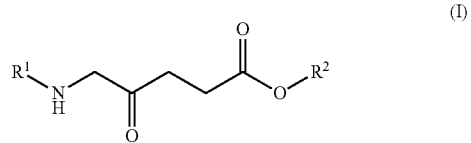

(I)

(wherein $R^1$ is a hydrogen atom or an acyl group, $R^2$ is a hydrogen atom, a linear or branched alkyl group, a cycloalkyl group, an aryl group, or an aralkyl group) or a salt thereof;

(2) the agent for ameliorating and/or preventing cancerous anemia according to (1) above, wherein $R^1$ and $R^2$ are hydrogen atoms;

(3) the agent for ameliorating and/or preventing cancerous anemia according to (1) or (2) above, further containing one or more metal-containing compounds;

(4) the agent for ameliorating and/or preventing cancerous anemia according to (3) above, wherein the metal-containing compound is a compound containing iron, magnesium, zinc, nickel, vanadium, copper, chrome, molybdenum, or cobalt;

(5) the agent for ameliorating and/or preventing cancerous anemia according to (3) above, wherein the metal-containing compound is a compound containing iron, magnesium, or zinc; and, (6) the agent for ameliorating and/or preventing cancerous anemia according to (3) above, wherein the metal-containing compound is a compound containing iron.

Also, the present invention relates to (7) a method for ameliorating and/or preventing cancerous anemia, the method comprising: administering a compound represented by formula (I) or a salt thereof; or administering a compound represented by formula (I) or a salt thereof and a metal-containing compound. As a different embodiment, the present invention relates to a compound represented by formula (I) or a salt thereof, or a compound represented by formula (I) or a salt thereof and a metal-containing compound for use in a method for ameliorating and/or a method for preventing cancerous anemia.

Effects of the Invention

By the agent for ameliorating and/or preventing cancerous anemia of the present invention, it is possible to achieve a superior amelioration and/or prevention effect for cancerous anemia, and the quality of life of cancer patients can be greatly improved with little or almost no side effects such as promotion of cancer growth.

DESCRIPTION OF EMBODIMENTS

In the present invention, cancerous anemia indicates all anemia occurring in cancer patients, and also includes anemia associated with bleeding in gastroenterological cancer or the like and anemia by side effects of anticancer drugs and radiation therapy. However, it is mainly cancer patient-specific anemia worsening with the development and progression as a part of cancer symptoms. Even in treatment field-work, the administration of erythropoietin, which is used for normal other anemic symptoms, is contraindicated. Cancerous anemia, different to other anemia, indicates not only reduction in red blood cells, but also indicates reduction in all normal blood cells differentiated from multifunctional hematopoietic stem cells, and also includes the reduction and decrease of white blood cells, lymphocytes, neutrophils, and blood platelets.

As a compound used as the active ingredient in the agent for ameliorating and/or preventing cancerous anemia of the present invention, a compound represented by formula (I) or a salt thereof (hereinafter, these are also collectively referred to as "ALAs") can be exemplified. ALA, also called δ-aminolevulinic acid, is when both $R^1$ and $R^2$ in formula (I) are hydrogen atoms, and is a type of an amino acid. As ALA derivatives, compounds other than ALA in which $R^1$ in formula (I) is a hydrogen atom or an acyl group and $R^2$ in formula (I) is a hydrogen atom, a linear or branched alkyl group, a cycloalkyl group, an aryl group, or an aralkyl group can be mentioned.

As the acyl group in formula (I), linear or branched alkanoyl groups having 1 to 8 carbon atoms such as formyl, acetyl, propionyl, butyryl, isobutyryl, valeryl, isovaleryl, pivaloyl, hexanoyl, octanoyl, and benzylcarbonyl; and aroyl groups having 7 to 14 carbon atoms such as benzoyl, 1-naphthoyl, and 2-naphthoyl groups can be mentioned.

As the alkyl group in formula (I), linear or branched alkyl groups having 1 to 8 carbon atoms such as methyl, ethyl, propyl, isopropyl, butyl, isobutyl, sec-butyl, tert-butyl, pentyl, isopentyl, neopentyl, hexyl, heptyl, and octyl groups can be mentioned.

As the cycloalkyl group in formula (I), cycloalkyl groups having 3 to 8 carbon atoms in which saturated or partially unsaturated bonds may be present such as cyclopropyl, cyclobutyl, cyclopentyl, cyclohexyl, cycloheptyl, cyclooctyl, cyclododecyl, and 1-cyclohexenyl groups can be mentioned.

As the aryl group in formula (I), aryl groups having 6 to 14 carbon atoms such as phenyl, naphthyl, anthryl, and phenanthryl groups can be mentioned.

As the aralkyl group in formula (I), the aryl portion can be the same as the above-mentioned aryl group examples and the alkyl portion can be the same as the above-mentioned alkyl group examples, and specifically, aralkyl groups having 7 to 15 carbon atoms such as benzyl, phenethyl, phenylpropyl, phenylbutyl, benzhydryl, trityl, naphthylmethyl, and naphthylethyl groups can be mentioned.

As the above-mentioned ALA derivative, a compound in which $R^1$ is formyl, acetyl, propionyl, or butyryl group, or the like, or a compound in which the above-mentioned $R^2$ is methyl, ethyl, propyl, butyl, or pentyl group, or the like is preferable; and a compound in which the combination of $R^1$ and $R^2$ is the combination of formyl and methyl, acetyl and methyl, propionyl and methyl, butyryl and methyl, formyl and ethyl, acetyl and ethyl, propionyl and ethyl, or butyryl and ethyl, or the like can be preferably mentioned.

For the ALAs, it is sufficient that they act as an active ingredient in vivo in the state of an ALA represented by formula (I) or a derivative thereof and it is sufficient that, according to the form of administration, they can be administered as various salts, esters, or prodrugs (precursors) decomposed by enzymes in the body, in order to enhance the solubility thereof. For example, as salts of ALA and a derivative thereof, pharmaceutically acceptable acid addition salts, metal salts, ammonium salts, organic amine addition salts, and the like can be mentioned. As the acid addition salts, various inorganic acid salts such as hydrochlorides, hydrobromates, hydroiodides, phosphates, nitrates, and sulfates; and various organic acid addition salts such as formates, acetates, propionates, toluenesulfonates, succinates, oxalates, lactates, tartrates, glycolates, methanesulfonates, butyrates, valerates, citrates, fumarates, maleates, and malates for example can be exemplified. As metal salts, various alkali metal salts such as lithium salts, sodium salts, and potassium salts; various alkali earth metal salts such as magnesium salts and calcium salts; and various metal salts such as those of aluminum and zinc can be exemplified. As ammonium salts, ammonium salts and alkyl ammonium salts such as tetramethyl ammonium salts can be exemplified. As organic amine salts, various salts such as triethyl amine salts, piperidine salts, morpholine salts, and toluidine salts can be exemplified. These salts may be used as a solution at the time of use.

Among the above-mentioned ALAs, ALA, various esters such as ALA methylester, ALA ethylester, ALA propylester, ALA butylester, and ALA pentylester, and hydrochlorides, phosphates and sulfates of these ALA esters are preferable, and ALA hydrochloride and ALA phosphate can be exemplified as particularly preferable.

The above-mentioned ALAs can be produced by any well-known method of chemical synthesis, production by microorganisms, and production by enzymes. Also, the above-mentioned ALAs may be in the form of a hydrate or a solvate and also, they may be used alone or by appropriately combining two or more thereof.

The agent for ameliorating and/or preventing cancerous anemia of the present invention preferably further contains a metal-containing compound in a range that does not cause excess symptoms. As the metal portion of such a metal-containing compound, iron, magnesium, zinc, nickel, vanadium, cobalt, copper, chrome, and molybdenum can be mentioned. Iron, magnesium, and zinc are preferable, and among these, iron can be preferably exemplified.

The above-mentioned iron compound may be an organic salt or an inorganic salt. As inorganic salts, ferric chloride, iron sesquioxide, iron sulfate, and ferrous pyrophosphate can be mentioned. As organic salts, organic acid salts such as carboxylates, for example, citrates such as ferrous citrate, sodium iron citrate, sodium ferrous citrate, and ammonium iron citrate, which are hydroxycarboxylates, ferric pyrophosphate, heme iron, iron dextran, iron lactate, ferrous gluconate, sodium iron diethylenetriaminepentaacetate, ammonium iron diethylenetriaminepentaacetate, sodium iron ethylenediaminetetraacetate, ammonium iron ethylenediaminepentaacetate, sodium iron dicarboxymethylglutamate, ammonium iron dicarboxymethylglutamate, ferrous fumarate, iron acetate, iron oxalate, ferrous succinate, and sodium iron succinate citrate, and iron triethylenetetramine, lactoferrin iron, transferrin iron, sodium iron chlorophyllin, ferritin iron, saccharated iron oxide, and ferrous glycine sulphate can be mentioned.

As the above-mentioned magnesium compound, magnesium citrate, magnesium benzoate, magnesium acetate, magnesium oxide, magnesium chloride, magnesium hydroxide, magnesium carbonate, magnesium sulfate, magnesium silicate, magnesium nitrate, diammonium magnesium diethylenetriaminepentaacetate, disodium magnesium ethylenediaminetetraacetate, and magnesium protoporphyrin can be mentioned.

As the above-mentioned zinc compound, zinc chloride, zinc oxide, zinc nitrate, zinc carbonate, zinc sulfate, diammonium zinc diethylenetriaminepentaacetate, disodium zinc ethylenediaminetetraacetate, zinc protoporphyrin, and zinc-containing yeast can be mentioned.

The above-mentioned metal-containing compounds can be used alone, or by combining two or more thereof. The dosage of the metal-containing compound may be 0 to 100 times the administered amount of ALA in molar ratio, and preferably 0.01 to 10 times, and more preferably 0.1 to 8 times.

The ALAs and the metal-containing compound contained in the agent for ameliorating and/or preventing cancerous anemia of the present invention can be administered as a composition containing the ALAs and the metal-containing compound or each separately. When each is separately administered, it is preferable that they are administered simultaneously. Herein, simultaneously means not only performed at the same time, but also performed, if not at the same time, without a considerable space between both so as administration of the ALAs and the metal-containing compound can achieve additive effects and preferably synergistic effects.

As the administration route of the agent for ameliorating and/or preventing cancerous anemia of the present invention, oral administration, also including sublingual administration; or parenteral administration such as inhalation administration, intravenous administration, also including an intravenous drip, transdermal administration by a cataplasm, a suppository, or administration by forced enteral nutrition using a nasogastric tube, a nasointestinal tube, a gastrostomy tube, or an enterostomy tube, or the like can be mentioned.

As the dosage form of the agent for ameliorating and/or preventing cancerous anemia of the present invention, although such can be appropriately determined according to the above-mentioned administration route, parenteral solutions, drops, tablets, capsules, fine granules, powder medicines, liquid formulations, liquid agents dissolved in a syrup or the like, cataplasms, and suppositories can be mentioned.

In order to prepare the agent for ameliorating and/or preventing cancerous anemia of the present invention, a pharmaceutically acceptable carrier, excipient, diluent, additive, disintegrant, binder, covering agent, lubricant, glidant, lubricating agent, flavoring agent, sweetener, solubilizer, solvent, gelling agent, and/or nutritional supplement can be added according to necessity. Specifically, water, normal saline solution, animal fats and oils, plant oils, lactose, starch, gelatin, crystalline cellulose, gum, talc, magnesium stearate, hydroxypropylcellulose, polyalkylene glycol, polyvinyl alcohol, and glycerin can be exemplified. When preparing the agent for ameliorating and/or preventing cancerous anemia of the present invention as an aqueous solution, in order to prevent degradation of the ALAs, it is necessary to take care so that the aqueous solution does not become alkaline. When the aqueous solution becomes alkaline, degradation can be prevented by removing oxygen.

As the amount, frequency, and period of administration of the agent for ameliorating and/or preventing cancerous anemia of the present invention, although such differ by the age, weight, symptoms, and the like of the cancerous anemia patient or the patient for which prevention of cancerous anemia is attempted, based on ALA molar conversion, 0.01 mmol to 25 mmol/day, preferably 0.025 mmol to 7.5 mmol/day, more preferably 0.075 mmol to 5.5 mmol/day, and further preferably 0.2 mmol to 2 mmol/day can be given as the administration amount of ALAs for one adult. Particularly, when used as a prevention agent, continued ingestion of a small amount is desirable. As the frequency of administration, administration one to several times per day or continuous administration by an intravenous drip or the like can be exemplified. As the administration period, when used as an amelioration agent, this can be determined by a known method by a pharmacologist or a clinician in the relevant technical field based on indicators showing the state of anemia such as red blood cell count, hemoglobin, white blood cell count, and blood platelets, and when used as a prevention agent, this can be determined by a known method by a pharmacologist or a clinician in the relevant technical field based on indicators showing the state of anemia such as red blood cell count, hemoglobin, white blood cell count, and blood platelets while observing so that worsening of cancerous anemia does not occur.

The agent for ameliorating and/or preventing cancerous anemia of the present invention can be used by combining with other known agents for ameliorating and/or preventing anemia. As known agents for ameliorating and/or preventing anemia, drugs such as iron supplements such as Ferromia, Ferrum, Ferro-Gradumet, Blutal, Slow-Fe, and Tetucur; vitamin supplements such as vitamin B12, vitamin folate and vitamin B6; and hematopoietic factor series such as human erythropoietin (EPO) and EPO derivatives in which a portion of the EPO sequence has been modified and a sugar chain has been added can be mentioned. Since it is considered that the mechanisms in connection with effects of ameliorating and preventing cancerous anemia regarding these drugs and ALA are fundamentally different, respectively, additive effects, and depending on the case, synergistic effects can be expected. Also, there is the possibility that when these known anemia drugs are used alone, they are useless in the amelioration of cancerous anemia or cancer is progressed. However, by combining them with the present invention, the effect of delaying cancer progression can also be expected.

Below, the present invention is more specifically explained by the Examples, but the technical scope of the present invention is not limited to these illustrations.

EXAMPLES

Example 1

For a woman suffering from scirrhous gastric cancer, the red blood cell count, the hemoglobin level, and the white blood cell count are shown in Table 1 below on (1) Feb. 16, 2008 (29 years old at this point) before suffering from the cancer, (2) Jul. 20, 2010, (3) Sep. 20, 2010 after starting the oral ingestion of 100 mg of aminolevulinic acid phosphate and 114.7 mg of sodium ferrous citrate daily from Aug. 19, 2010, when it was discovered she was suffering from the cancer, (4) Oct. 12, 2010, (5) Jan. 13, 2011, and (6) Jul. 1, 2011.

TABLE 1

| | Red blood cell count ($\times 10^6/\mu L$) | Hemoglobin (g/dL) | White blood cell count ($\times 10^3/\mu L$) |
|---|---|---|---|
| 2008 Feb. 16 | 4.48 | 13.10 | 4.40 |
| 2010 Jul. 20 | 3.93 | 10.60 | 4.00 |
| 2010 Sep. 20 | 3.51 | 9.70 | 2.70 |
| 2010 Oct. 12 | 3.53 | 10.50 | 5.10 |
| 2011 Jan. 13 | 3.63 | 11.80 | 4.10 |
| 2011 Jul. 01 | 3.58 | 11.60 | 5.50 |

From Table 1 above, all of the anemia-related hematological indicators as the red blood cell count, the hemoglobin level, and the white blood cell count, which were normal values before suffering from the cancer, reduced by suffering from the cancer and she became cancerous anemia. However, she spectacularly recovered by the administration of aminolevulinic acid phosphate and sodium ferrous citrate. After it was understood that the patient was suffering from the cancer, she received anticancer drug treatment (TS1+docetaxel therapy was performed. On the first day, 54 mg/day of docetaxel by intravenous drip, 100 mg/day of TS1 orally for 14 days, and 7 days of drug cessation. One course was performed for 21 days.) Although it is considered that normally anemia will proceed as a side effect of anticancer drugs, anemia was resolved by the ingestion of ALA and the iron compound, and thus such overcoming of cancerous anemia is astounding.

Example 2

On Aug. 19, 2009 (61 years old at this point), emergency surgery was performed on a woman in which an intestinal obstruction occurred due to the advanced stage of colon cancer. Through observation at the time of surgery, it was found that there was colon cancer the size of a fist. Although the cancer was removed and the intestinal obstruction was released, it was accepted that there are multiple peritoneal disseminations, and she received the diagnosis of a life expectancy of 3 months. After surgery, as anticancer drug treatment, in addition to FOLFOX (combined use of the three agents 5-FU, Isovorin, and Elplat) and FOLFIRI (combined use of the three agents 5-FU, Isovorin, and Campto), a molecular target drug such as Avastin was used in combination. Also, in parallel with such anticancer drug treatment, daily 50 mg of aminolevulinic acid phosphate and 57.4 mg of sodium ferrous citrate were ingested orally. As a result, the anticancer drug treatment was able to be continued for one year after surgery. Although administration of the anticancer drugs was abandoned one year after surgery due to side effects, oral administration of 50 mg of aminolevulinic acid phosphate and 57.4 mg of sodium ferrous citrate was continued. The patient, largely exceeding the notified life expectancy of 3 months, was as able to exist in the state of improved side effects for a year and a half.

The red blood cell count, the hemoglobin level, and the white blood cell count are shown in Table 2 below on (i) Aug. 19, 2009 directly before surgery and (ii) Jan. 28, 2011, which is about the one year and five months after starting ingestion of aminolevulinic acid phosphate and sodium ferrous citrate.

TABLE 2

|  | Red blood cell count ($\times 10^6/\mu L$) | Hemoglobin (g/dL) | White blood cell count ($\times 10^3/\mu L$) |
|---|---|---|---|
| 2009 Aug. 19 | 2.97 | 9.80 | 13.20 |
| 2011 Jan. 28 | 3.44 | 12.20 | 6.20 |

From Table 2 above, although reduction in the red blood cell count and hemoglobin by cancerous anemia and increase in the white blood cell by inflammation can be seen directly before surgery, at (ii) the point of about one year and five months after the start of the ingestion, the red blood cell count and hemoglobin increased by the administration of aminolevulinic acid phosphate and sodium ferrous citrate, and thus anemia was improved. Also, the white blood cell count fell to the normal level. When it is considered that there were strong side effects by the anticancer drugs, it can be considered that strong damage is caused to the hematopoietic system. However, the result of anemia improving is astounding, and while having peritoneal disseminations, the patient has been able to lead a life with improved quality of life for a year and a half, largely exceeding the doctor's notified life expectancy of 3 months.

Example 3

An 83 year-old woman suffering from chronic lymphatic leukemia received treatment by the anticancer drug Rituxan. After treatment, daily 150 mg of aminolevulinic acid phosphate and 172 mg of sodium ferrous citrate were ingested orally. The white blood cell count, the red blood cell count, the hemoglobin, and the blood platelet count before and after treatment are shown in Table 3 below.

TABLE 3

|  | Red blood cell count ($\times 10^6/\mu L$) | Hemoglobin (g/dL) | White blood cell count ($\times 10^3/\mu L$) | Blood platelet count ($\times 10^3/\mu L$) |
|---|---|---|---|---|
| 2010 Jan. 13 | 3.27 | 9.70 | 16.48 | 103.00 |
| 2010 Nov. 22 | 2.80 | 9.20 | 1.56 | 101.00 |
| 2011 May 20 | 3.18 | 9.90 | 1.37 | 160.00 |

TABLE 3-continued

|  | Red blood cell count ($\times 10^6/\mu L$) | Hemoglobin (g/dL) | White blood cell count ($\times 10^3/\mu L$) | Blood platelet count ($\times 10^3/\mu L$) |
|---|---|---|---|---|
| 2011 Jun. 24 | 3.13 | 9.80 | 3.47 | 127.00 |
| 2011 Aug. 05 | 3.01 | 9.70 | 3.41 | 142.00 |

From Table 3 above, although it is understood from the examination value on Jan. 13, 2010 that it is leukemia because it was seen that the white blood cell count increased, it is understood that cancerous anemia occurred from simultaneously also the red blood cell count, the hemoglobin, and the white blood cell count deteriorating. From Nov. 15, 2010, anticancer drug treatment by Rituxan began, and although reduction in the white blood cell count was observed as early as Nov. 22, 2010 after one cycle of the anticancer drug treatment, simultaneously the red blood cell count, the hemoglobin, and the blood platelet count decreased, and thus it is considered that anemia progressed as a side effect.

The anticancer drug treatment was completed on Mar. 16, 2011. Although there are no examination values at the point of completion, it is conceived that anemia further progressed. The daily oral ingestion of aminolevulinic acid phosphate and sodium ferrous citrate was started from this point, and from examination on May 20 after about the passing of two months, significant restoration was seen in red blood cells, hemoglobin, and blood platelets, and the blood platelet count returned to the normal level. What is notable is the white blood cell count. While white blood cell count normally decreases when the white blood cell count is suppressed by Rituxan in the treatment of leukemia and it often poses a problem for immunity without recovery as it stands, the possibility of recurrence is high if the dosage of the anticancer drug is reduced. From Table 3, it is clear that while sufficiently reducing the white blood cell count, there was the very good progression of recovery after this. There are almost no such clinical examples, and thus these results can be said to be the effect of the administration of ALA and the iron compound. Although anemia normally means insufficiency of white blood cells and hemoglobin, there is no change to the fact that white blood cells and red blood cells are cells from differentiation of hematopoietic stem cells, and thus it is suggested that the effect of improving cancerous anemia of ALA is an effect which was not known so far.

INDUSTRIAL APPLICABILITY

The agent for ameliorating and/or preventing cancerous anemia of the present invention can be advantageously utilized in the medical field.

The invention claimed is:

1. A method for ameliorating and/or preventing cancerous anemia, the method comprising administering to a subject having cancerous anemia an agent comprising a compound represented by the following formula (I) or a salt thereof:

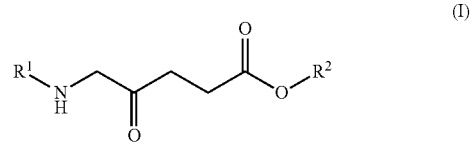

(I)

wherein $R^1$ and $R^2$ are hydrogen atoms, and
wherein the subject is a patient with cancer who is characterized by both reduction of red blood cells and reduction of at least one selected from lymphocytes, neutrophils, and blood platelets.

2. The method according to claim 1, wherein the agent further comprises one or more metal-containing compounds.

3. The method according to claim 2, wherein the metal-containing compound is a compound containing iron, magnesium, zinc, nickel, vanadium, copper, chrome, molybdenum, or cobalt.

4. The method according to claim 2, wherein the metal-containing compound is a compound containing iron, magnesium, or zinc.

5. The method according to claim 2, wherein the metal-containing compound is a compound containing iron.

6. The method according to claim 1, wherein the agent further comprises one or more metal-containing compounds.

7. The method according to claim 6, wherein the one or more metal-containing compound is a compound containing iron, magnesium, zinc, nickel, vanadium, copper, chrome, molybdenum, or cobalt.

8. The method according to claim 6, wherein the one or more metal-containing compound is a compound containing iron, magnesium, or zinc.

9. The method according to claim 6, wherein the one or more metal-containing compound is a compound containing iron.

10. The method according to claim 1, wherein the cancer is leukemia.

\* \* \* \* \*